United States Patent [19]

Hershenson

[11] Patent Number: 4,585,000
[45] Date of Patent: Apr. 29, 1986

[54] EXPANDABLE DEVICE FOR TREATING INTRAVASCULAR STENOSIS

[75] Inventor: Harold Hershenson, Coral Gables, Fla.

[73] Assignee: Cordis Corporation, Miami, Fla.

[21] Appl. No.: 537,248

[22] Filed: Sep. 28, 1983

[51] Int. Cl.[4] .......................................... A61M 29/00
[52] U.S. Cl. ................................. 128/345; 604/108; 604/109
[58] Field of Search ................... 128/344, 345; 604/52, 604/53, 100, 104, 105, 106, 108, 109, 96, 102, 103, 170, 209, 211, 212, 224

[56] References Cited

U.S. PATENT DOCUMENTS

| | | | |
|---|---|---|---|
| 297,263 | 4/1984 | Hunt | 604/108 |
| 1,089,061 | 2/1912 | Kistler | 604/108 |
| 1,267,066 | 5/1918 | Flack | 128/345 |
| 1,331,737 | 2/1920 | Ylisto | 128/345 |
| 2,649,092 | 8/1953 | Wallace . | |
| 2,689,568 | 9/1954 | Wakefield | 128/345 |
| 3,397,699 | 8/1968 | Kohl . | |
| 3,557,794 | 1/1971 | Van Patten | 128/345 |
| 3,568,659 | 3/1971 | Karnegis . | |
| 3,667,474 | 6/1972 | Lapkin et al. | 128/345 |
| 4,228,802 | 10/1980 | Trott . | |
| 4,292,974 | 10/1981 | Fogarty et al. | 604/53 |
| 4,299,226 | 11/1981 | Banka | 604/53 |
| 4,362,150 | 12/1982 | Lombardi, Jr. et al. . | |
| 4,364,392 | 12/1982 | Strother et al. . | |
| 4,422,447 | 12/1983 | Schiff . | |

Primary Examiner—C. Fred Rosenbaum
Assistant Examiner—Mark Rooney
Attorney, Agent, or Firm—Henry W. Collins; Thomas R. Vigil

[57] ABSTRACT

The intravascular expandable device is adapted to be inserted within and through the lumen of a blood vessel and to be manipulated therethrough to a stenotic area where it can be operated for re-establishing desired blood flow through the blood vessel. The device comprises an elongate tubular body having a distal end and a proximal end, an expandable pressure applying assembly including a flexible tubular member mounted to the distal end of the tubular body and a mechanism operable to expand the tubular member outwardly. A tip member is connected to the distal end of the flexible tubular member and an expansion and retraction control mechanism is coupled to the pressure applying assembly for expanding, maintaining expanded or retracting the flexible tubular member relative to a stenotic area within the blood vessel. Preferably, passage means are provided around or through the pressure applying assembly in the device so that the flow of blood through the vessel is not interrupted.

The method for treating intravascular stenosis in a blood vessel includes the steps of first inserting the expandable pressure applying assembly into and through the lumen of a blood vessel for applying pressure to the vessel wall, second, manually manipulating the expandable pressure applying assembly into and through the lumen of the blood vessel to a position within a surrounding area of intravascular stenosis, thirdly, operating the expandable pressure applying assembly to expand an expandable tubular member against the surrounding intravascular stenosis, and fourthly, maintaining the expanded tubular member against the vessel wall of the blood vessel for a predetermined time period in order to dilate the vessel and restore it to its normal diameter.

22 Claims, 4 Drawing Figures

EXPANDABLE DEVICE FOR TREATING INTRAVASCULAR STENOSIS

BACKGROUND OF THE INVENTION

1. Field of the Invention

The present invention relates to a pressure applying device and method for using the device for treating intravascular stenosis within a blood vessel in order to restore necessary blood flow therethrough. The device includes an expandable intravascular pressure applying mechanism which is positionable in an area of surrounding intravascular stenosis within a blood vessel and operable to apply surface pressure against the inner wall of the stenotic blood vessel in order to dilate the vessel and restore it to a diameter closer to its normal diameter.

2. Description of the Prior Art

Heretofore various expandable devices have been proposed such as a so-called balloon catheter having a balloon mounted to the distal end of the catheter. The balloon is inserted into a vessel and inflated to a high pressure with the infusion of liquid. As a result once a balloon has been inflated in a vessel, flow of blood through the vessel is stopped.

Since vessels vary in thickness, a balloon catheter having a balloon of one size may require multiple balloons for one procedure. Also, the balloon itself may not be smooth when deflated and thus difficult to remove from or insert into a blood vessel.

Another system for dilating an area of intravascular stenosis includes two catheters, one slidably received over the other. In use, the smaller catheter is inserted into the vessel. Then the longer catheter is slid over the smaller catheter and, when it reaches the area of intravascular stenosis, it forces the stenotic area outwardly thereby to dilate the vessel in the area of intravascular stenosis.

Other such devices also have been proposed which have expanding splines or ribs which extend outwardly from the surface of a catheter. Examples of such previously proposed devices are disclosed in the following U.S. Patents:

| U.S. Pat. No. | PATENTEE |
|---|---|
| 2,649,092 | Wallace |
| 3,397,699 | Kahl |
| 3,568,659 | Karnegis |
| 4,228,802 | Trott |
| 4,362,150 | Lombardi, Jr. et al |
| 4,364,392 | Strother et al |

The Wallace U.S. Pat. No. 2,649,092 discloses a catheter which is adapted to be employed in various urological procedures and which has circumferentially spaced longitudinal slots adjacent the forward end thereof. The portions of the catheter between the extremities of the slots are flexible and outwardly distortable when the forward end of the catheter is retracted with respect to the rearward end by means of a flexible member anchored to the forward end to cause such portions to exert pressure against the inner surface of a urethra in which the catheter has been inserted.

The Kahl U.S. Pat. No. 3,397,699 discloses a bladder catheter having a plurality of longitudinal slits distributed about a circumferential zone adjacent to an aperture at a distal end of the catheter. The longitudinal slits define therebetween a plurality of outwardly foldable wing elements formed when the proximal and distal ends of the circumferential zone or cylindrical envelope are drawn together by means of some resilient elastic means, such as rubber elements, located on the interior wall of the catheter and spanning the wing elements longitudinally. The catheter is adapted to receive therein a stylet which is inserted through an open proximal end of the catheter and is manipulated to draw the wing elements inward for insertion and removal of the catheter. When the catheter is positioned in a body cavity, particularly the bladder, the stylet is withdrawn allowing the wing elements to fold outwardly, retaining the expanded circumferential zone of the catheter in position.

The Karnegis U.S. Pat. No. 3,568,659 discloses an intercardiac heart pump comprising a catheter having on its extremity an expandable and contractable member. The catheter has a series of resilient, flexible ribs spaced about the catheter and parallel to the catheter's axis. One end of each rib is secured to the catheter adjacent the catheter tip, while the other end of each rib is anchored to a ring connected to a reciprocating member within the catheter which is slidably supported on the catheter. The ribs are encircled by a resilient tube which is anchored to the catheter beyond the ends of the ribs. When the reciprocating member is moved forward in the catheter, the flexible ribs are caused to bow outwardly, expanding the resilient tube which encircles the ribs. The expandable part of the catheter can be positioned within the left ventricle. When the ribs are flexed from a position generally parallel to the catheter in an outwardly bowed position, the resilient tube can be expanded to more or less fill the left ventricle.

The Trott U.S. Pat. No. 4,228,802 discloses a bladder catheter with a mechanical expanding device near the distal end thereof which can be operated by an actuator near the proximal external end thereof. The catheter comprises a pair of tubes, one within the other, forming a pair of interior lumina. The inner cylindrical lumen serves as a drainage channel and the second outer lumen formed by the cross sectional space between the two tubes provides a passage for irrigating fluids. Adjacent the distal end of the outer tube are a plurality of traversely notched splines on the inside of the outer tube extending longitudinally. parallel to the axis of the catheter. The outer tube can be moved rearward relative to the inner tube, thereby causing the splines to flex outwardly and expanding the outer tube in the area of the splines.

The outer tube is moved by means of a threaded advancing nut assembly including an annular flange formed on the proximal end of the outer tube, a screw threaded portion along the length of the inner tube, and an internally threaded nut which threadably engages the threaded portion on the inner tube and frictionally engages the annular flange on the outer tube. Rotation of the nut moves the outer tube rearwardly, flexing the splines outwardly and expanding the outer tube.

In the expanded position, the catheter is retained in position in the bladder. The inner tube also contains an auger-like spiral screw to prevent blood clots and debris from blocking the drainage.

The Lombardi, Jr., et al. U.S. Pat. No. 4,362,150 discloses an intra-aortic balloon pump attached to the end of a catheter. The proximal end of the balloon is bonded to the distal end of the catheter while the distal end of the balloon is bonded to the distal end of a rotatable tube within and extending the length of the catheter. The rotatable tube is longitudinally flexible and circumferentially rigid so that when a torque is applied to the proximal end, the torque is transmitted the length of the tube to the balloon. When the tube is rotated, the balloon is wrapped for insertion into the aorta and unwrapped for pumping, then rewrapped for removal, the balloon itself being pumped in a conventional manner via a lumen within the catheter.

The Strother et al U.S. Pat. No. 4,364,392 discloses a method and apparatus for providing therapeutic occlusions to blood vessels using an inflatable balloon mounted at the end of a catheter.

As will be described in greater detail hereinafter, the device for treating intravascular stenosis of the present invention differs from the devices previously proposed by having therein a catheter with an expandable pressure applying mechanism. The pressure applying mechanism is screw activated and provides a number of advantages, such as providing a variety of expansion sizes to accommodate varying sizes of blood vessels. An expanding mechanism that cannot burst like a balloon, and a mechanism which can be collapsed to conform closely to the diameter of the catheter to minimize trauma upon insertion and withdrawal of the device into and from a blood vessel.

Further, there is provided in the device passageways which allow the flow of blood into, through and around the expandable pressure applying mechanism for an extended period of time while the blood vessel is being dilated by the device so that the flow of blood is not interrupted.

SUMMARY OF THE INVENTION

According to the invention there is provided a method for treating intravascular stenosis in a blood vessel utilizing an intravascular expandable device comprising: an elongate tubular body having a proximal end, a distal end and a central bore therethrough; expandable pressure applying means including a flexible tubular member extending from said distal end of said tubular body and a mechanical mechanism within said flexible tubular member capable of engaging and expanding said tubular member radially outwardly only; a tip member connected to the distal end of said flexible tubular member; said mechanism including a nut with an axis coaxial with the axis of said tubular member, a plurality of curved-in-cross-section elongate baffles, a plurality of linkages, each baffle being pivotally connected by one of said linkages to said nut, said nut having threads therein, a threaded rod extending axially through said bore and being journaled to said tubular body or to said tip member, being received through said nut and being capable of causing axial movement of said nut when rotated to cause each linkage to move one of said baffles outwardly to expand said tubular member, a rotatable bushing on said threaded rod adjacent the distal end thereof for limiting axial movement of said nut on said threaded rod, each linkage including an arm pivotally connected at one end to said hub and pivotally connected at the other end to the underside of one of said baffles, and a strut pivotally connected to said bushing and to one of said arms intermediate the ends thereof, and expansion and retraction control means coupled to said mechanical mechanism for causing said mechanism to expand said flexible tubular member, to maintain said flexible tubular member expanded and to allow said flexible tubular member to retract within a stenotic area in a blood vessel, comprising the steps of: inserting the expandable device into and through the lumen of a blood vessel; positioning the expandable pressure applying means of the device within a surrounding area of vascular stenosis; mechanically expanding the expandable pressure applying means to cause same to bear against the surrounding area of intravascular stenosis; providing passage means bypassing the pressure applying means to allow blood to flow through or around the pressure applying means while it is expanded; and maintaining the mechanical pressure of the expanded pressure applying means against the vessel wall for a predetermined time period of from one to five minutes in order to dilate the stenoic stricture and restore the vessel to its normal diameter.

Further according to the invention, there is provided an intravascular expandable device adapted to be inserted within and through the lumen of a blood vessel and manipulatable therethrough to a stenotic area where it can be operated for re-establishing desired blood flow through the blood vessel, said device comprising: an elongate tubular body having a proximal end, a distal end and a central bore therethrough, expandable pressure applying means including a flexible tubular member extending from said distal end of said tubular body and a mechanical mechanism within said flexible tubular member capable of engaging and expanding said tubular member radially outwardly only; a tip member connected to the distal end of said flexible tubular member; said mechanism including a nut with an axis coaxial with the axis of said tubular member, a plurality of curved-in-cross-section elongate baffles, a plurality of linkages, each baffle being pivotally connected by one of said linkages to said nut, said nut having threads therein, a threaded rod extending axially through said bore and being journaled to said tubular body or to said tip member, being received through said nut and being capable of causing axial movement of said nut when rotated to cause each linkage to move one of said baffles outwardly to expand said tubular member, a rotatable bushing on said threaded rod adjacent the distal end thereof for limiting axial movement of said nut on said threaded rod, each linkage including an arm pivotally connected at one end to said hub and pivotally connected at the other end to the underside of one of said baffles, and a strut pivotally connected to said bushing and to one of said arms intermediate the ends thereof, and expansion and retraction control means coupled to said mechanical mechanism for causing said mechanism to expand said flexible tubular member, to maintain said flexible tubular member expanded and to allow said flexible tubular member to retract within a stenotic area.

DESCRIPTION OF THE PREFERRED EMBODIMENT

Figure 1:
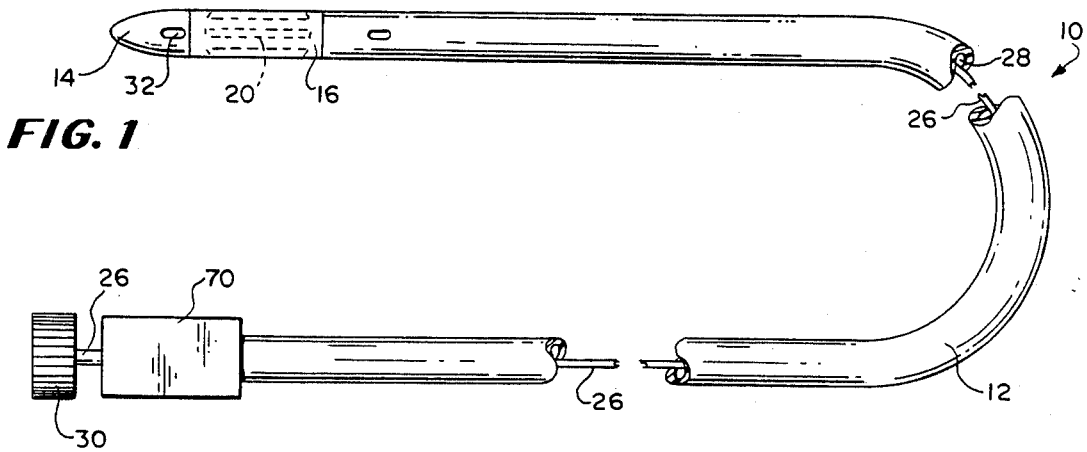
FIG. 1 is a plan view of the intravascular expandable device of the present invention and shows portions thereof broken away to a flexible shaft extending through the tubular body of the device.

Referring now to FIG. 1, there is illustrated therein an intravascular expansion device of the present invention generally identified by reference numeral 10. According to the teachings of the present invention, the device 10 is adapted to be inserted into and through the lumen of a blood vessel and manipulatable therethrough to a position within an area of intravascular stenosis. Then an expandable pressure applying mechanism 11 (FIG. 2) can be operated to dilate the stenotic vessel.

The device 10 also includes an elongate thick walled tubular body or catheter 12, a hollow conical tip member 14, and an expandable, flexible tubular member 16 which is mounted therebetween and which forms part of the pressure applying mechanism 11. The tip member 14 and the tubular body 12 are made of a material that is relatively rigid relative to the expandable flexible tubular member 16 and yet flexible enough to allow the device 10 to be manipulated through a blood vessel.

Figure 4:
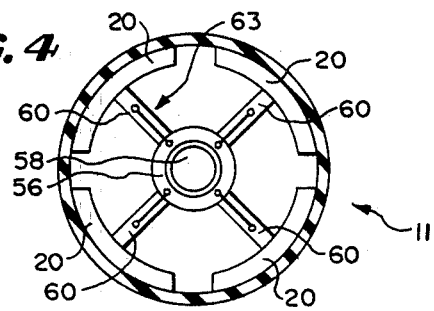
FIG. 4 is a cross sectional view of the intravascular expandable device through the expandable pressure applying mechanism and is taken along line 4—4 of FIG. 2.

The expandable pressure applying mechanism 11 (FIG. 2) is mounted within a hollow distal end portion 17 of the tubular body 12 and within the flexible tubular member 16 and includes four curved in cross-section, elongate baffles 20 (FIG. 2) which define a generally cylindrical envelope (FIG. 4). The baffles 20 extend approximately the length of the expandable tubular member 16.

The expandable pressure applying mechanism 11 also includes and is controlled by a flexible shaft or stylet 26 which extends through the tubular body 12 through a bore 28 therein. A control knob 30 is connected to the proximal end of the shaft 26. The knob 30 and shaft 26 define a control mechanism for the pressure applying mechanism 11.

The tip member 14 has a plurality of, e.g., four, ports 32 and the tubular body 12 has a plurality of, e.g., four, ports 34 in the hollow distal end portion 17 which facilitate the flow of blood around or through the pressure applying mechanism 11 and through the vessel when the pressure applying mechanism 11 is expanded in the vessel. This construction permits the pressure applying mechanism 11 to be expanded in a blood vessel without interrupting the flow of blood so that a physician, or whoever is operating the pressure applying mechanism 11, may maintain the pressure applying mechanism 11 expanded in the blood vessel for an extended period of time, if necessary, without interrupting the flow of blood.

Figure 2:
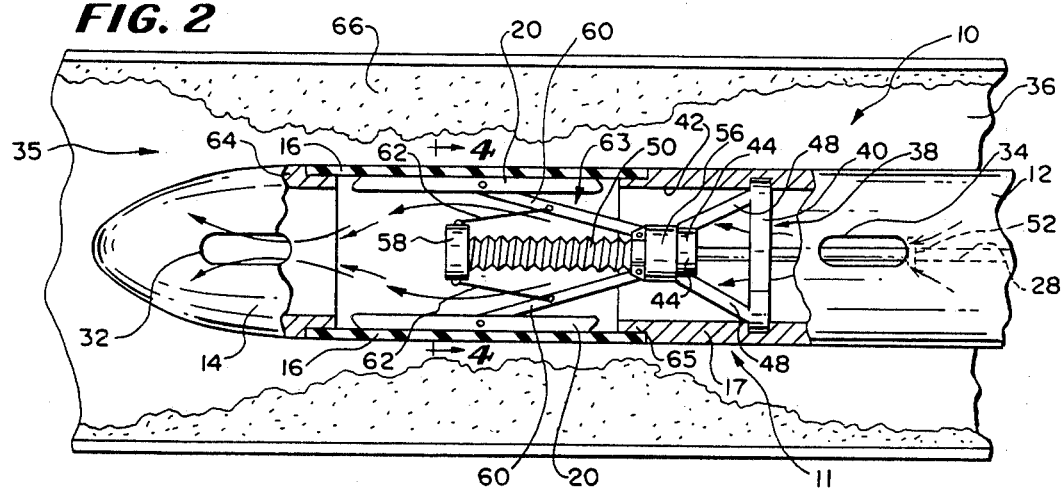
FIG. 2 is a vertical sectional view of the distal end of the intravascular expandable device of FIG. 1 positioned in a blood vessel in an area of surrounding intravascular stenosis and shows an expandable pressure applying mechanism of the device retracted.
Figure 3:
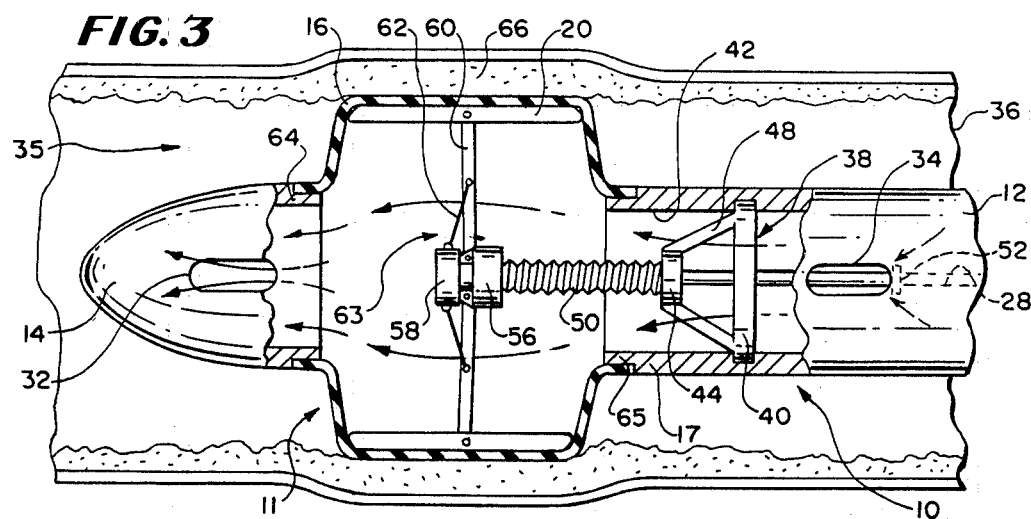
FIG. 3 is a vertical sectional view of the distal end of the intravascular expandable device and shows the expandable pressure applying mechanism expanded and bearing against the stenotic area of the blood vessel.

Referring now to FIG. 2, the expandable pressure applying mechanism 11 of the device 10 is shown positioned in an area of intravascular stenosis 35 in a blood vessel 36, with baffles 20 in a retracted position.

The pressure applying mechanism 11 includes a hub 38 having an annular base 40 circumferentially mounted to an inner wall 42 of the tubular body 12 in the hollow distal end portion 17 thereof.

The hub 38 further includes a collar 44 and four legs 48 between the base 40 and collar 44. A threaded rod 50 is rotatably mounted or journalled within the collar 44 and the distal end of the flexible shaft 26 is fixed to the proximal end of the threaded rod 50 which is journalled in the collar 44. At the proximal end of hollow distal end portion 17 a seal 52 is provided between shaft 26 and bore 28.

The expandable pressure applying mechanism 11 further includes a barrel or nut 56 which is threadedly mounted on a rod 50. The threaded rod 50 has a bushing 58 journalled on the distal end thereof for limiting axial movement of the nut 56 thereon. If desired, the rod 50 can extend past or beyond the bushing 58 and be journalled in a bracket, not shown, fixed within tip member 14. Four arms 60 are pivotably connected to the nut 56 and pivotably connected to the underside of one of the baffles 20. Also four restraining struts 62 are provided, each being pivoted at one end to one of the arms 60 approximately midway between the ends thereof and at the other end to rotatable bushing 58. Each arm 60 and strut 62 forms a movable linkage 63.

The flexible tubular expandable member 16 is fixed to a shoulder 64 at the proximal end of the conical tip member 14 and to a shoulder 65 at the distal end of tubular body 12 with a continuous, smooth outer surface then being provided on the periphery of the device 10 when the expandable member 16 is collapsed. The expandable member 16 is made from a material which is easily expandable beyond the diameter of the tip member 14 and the tubular body 12. In this respect, the member 16 can be a tubular section of approximately 0.002 mm thick silicone rubber, polyurethane or other suitable biocompatible polymer.

In operating the device 10, the expandable mechanism 11 is first positioned in a stenotic area 35. Then, the control know 30 is rotated to rotate shaft 36 and threaded rod 50 thereby to advance the nut 56 to cause the rods 60 to move outwardly and force the baffles 24 against the flexible tubular member 16 to increase the diameter thereof. As the threaded nut 56 traverses the threaded rod 50, the arms 60 extend further outwardly and finally to a position perpendicular to the threaded rod 50 to dilate a stenotic stricture 66 in the stenotic area 35.

In order to obtain the desired dilation of the stenotic stricture 66 to restore the vessel 36 to its normal inner diameter, various diameters of the expandable member 16 can be utilized, depending upon the particular vessel being treated and dependent upon what is shown by fluoroscopy or other imaging technique employed. Also, the knob 30 will have calibration markings or an indicator thereon relative to an indicator or calibration markings on an adjacent block or sleeve 70 on the distal end of the tubular body 12 to indicate to a user the amount of dilation for a fractional rotation of the knob 30.

For example, a coronary vessel requires the device 10 to have an unexpanded diameter of preferably no more than 1.35 mm and be expandable up to approximately 4.00 mm in diameter. On the other hand, periphery vessels require the device 10 to have an unexpanded diameter of preferably no more than 2.3 mm and be expandable up to approximately 8 mm in diameter.

Typically, the tubular body or catheter 12 has a diameter approximately one-third the diameter of the blood vessel into which it is inserted. Such a diameter will typically be between 1 mm and 3 mm and one preferred diameter is 1.35 mm. Another preferred diameter is 2.3 mm.

After a predetermined period of time, the expandable pressure applying mechanism 11 is withdrawn from the stenotic area 35 and a contrast medium can be introduced into the blood vessel 36 in order to determine whether or not the stenotic stricture 66 has been reduced as a result of the dilation of the blood vessel 36. The contrast medium is typically a fluoroscopically detectable material which is radiographically monitored by monitoring the flow of blood through the area 35 of stenosis. Once it has been determined that the stenosis 35 has been reduced and blood flow therethrough has returned to normal, the device 10 is removed from the vessel 36.

Another technique for determining the extent of dilation of the stenotic area in the blood vessel is by measuring the pressure on each side of the formerly restricted intervascular stenotic area. This is accomplished with a pressure sensing catheter device which is inserted in the vessel and which is then utilized to measure pressure upstream and downstream of the area where the intravascular stenosis was located. Small or no differences in pressure then indicate effective dilation of the stenotic area.

Typically the holding time of the expandable mechanism 11 in a blood vessel is 1 to 5 minutes.

From the foregoing description it will be apparent that the device 10 of the present invention provides a number of advantages, some of which have been described above and others of which are inherent in the invention. In particular, the expandable pressure applying mechanism 11 will not burst and can collapse to conform closely to the diameter of the device 10 rendering insertion and withdrawal less traumatic.

Further the expandable pressure applying mechanism 11 can accommodate various diameter blood vessels because of the screw-activated adjustment which may vary from 1.35 mm to 8.0 mm, depending upon the size of the vessel being treated.

Still further, ports 32 and 34 provide means through which blood may flow to permit the device 10 to be positioned in the stenotic area for an extended period of time for maintaining the stenotic stricture 66 dilated without interfering with the flow of blood therethrough.

Also it will be apparent to those skilled in the art that modifications can be made to the device 10 of the present invention without departing from the teachings of the invention.

Accordingly, the scope of the invention is only to be limited as necessitated by the accompanying claims.

I claim:

1. A method for treating intravascular stenosis in a blood vessel utilizing an intravascular expandable device comprising: an elongate tubular body having a proximal end, a distal end and a central bore therethrough; expandable pressure applying means including a flexible tubular member extending from said distal end of said tubular body and a mechanical mechanism within said flexible tubular member capable of engaging and expanding said tubular member radially outwardly only; a tip member connected to the distal end of said flexible tubular member; said mechanism including a nut with an axis coaxial with the axis of said tubular member, a plurality of curved-in-cross-section elongate baffles, a plurality of linkages, each baffle being pivotally connected by one of said linkages to said nut, said nut having threads therein, a threaded rod extending axially through said bore and being journaled to said tubular body or to said tip member, being received through said nut and being capable of causing axial movement of said nut when rotated to cause each linkage to move one of said baffles outwardly to expand said tubular member, a bushing on said threaded rod adjacent the distal end thereof for limiting axial movement of said nut on said threaded rod, each linkage including an arm pivotally connected at one end to said nut and pivotally connected at the other end to the underside of one of said baffles, and a strut pivotally connected to said bushing and to one of said arms intermediate the ends thereof, and expansion and retraction control means coupled to said mechanical mechanism for causing said mechanism to expand said flexible tubular member, to maintain said flexible tubular member expanded and to allow said flexible tubular member to retract within a stenotic area in a blood vessel, comprising the steps of: inserting the expandable device into and through the lumen of a blood vessel; positioning the expandable pressure applying means of the device within a surrounding area of vascular stenosis; mechanically expanding the expandable pressure applying means to cause same to bear against the surrounding area of intravascular stenosis; providing passage means bypassing the pressure applying means to allow blood to flow through or around the pressure applying means while it is expanded; and maintaining the mechanical pressure of the expanded pressure applying means against the vessel wall for a predetermined time period of from one to five minutes in order to dilate the stenoic stricture and restore the vessel to its normal diameter.

2. The method of claim 1 further including the steps of: introducing contrast material into the blood vessel; fluoroscopically monitoring the contrast material through the area of stenosis to determine the extent of stenotic reduction; and subsequently retracting and removing the expandable pressure applying means from the vessel.

3. The method of claim 2 wherein the expandable pressure applying means are removed when the flow of contrast material indicates uninterrupted blood flow through the formerly stenotic area.

4. An intravascular expandable device adapted to be inserted within and through the lumen of a blood vessel and manipulatable therethrough to a stenotic area where it can be operated for re-establishing desired blood flow through the blood vessel, said device comprising: an elongate tubular body having a proximal end, a distal end and a central bore therethrough, expandable pressure applying means including a flexible tubular member extending from said distal end of said tubular body and a mechanical mechanism within said flexible tubular member capable of engaging and expanding said tubular member radially outwardly only; a tip member connected to the distal end of said flexible tubular member; said mechanism including a nut with an axis coaxial with the axis of said tubular member, a plurality of curved-in-cross-section elongate baffles, a plurality of linkages, each baffle being pivotally connected by one of said linkages to said nut, said nut having threads therein, a threaded rod extending axially through said bore and being journaled to said tubular body or to said tip member, being received through said nut and being capable of causing axial movement of said nut when rotated to cause each linkage to move one of said baffles outwardly to expand said tubular member, a bushing on said threaded rod adjacent the distal end thereof for limiting axial movement of said nut on said threaded rod, each linkage including an arm pivotally connected at one end to said nut and pivotally connected at the other end to the underside of one of said baffles, and a strut pivotally connected to said bushing and to one of said arms intermediate the ends thereof, and expansion and retraction control means coupled to said mechanical mechanism for causing said mechanism to expand said flexible tubular member, to maintain said flexible tubular member expanded and to allow said flexible tubular member to retract within a stenotic area.

5. The device of claim 4 wherein said tip member, said expandable pressure applying means and the distal end of said tubular body have passage means for facilitating flow of blood through the device and back into the blood vessel.

6. The device of claim 5 wherein said tip member and the distal end of said tubular body are hollow and said passage means include at least one port in the wall of said tip member and at least one port in the wall of said tubular body at the distal end thereof to permit liquid flow through said tip member, said flexible expandable tubular member and said tubular body while a stenotic area is being dilated by said expandable pressure applying means.

7. The device of claim 4 wherein said expansion and retraction control means include a flexible rotatable shaft within said central bore of said tubular body.

8. The device of claim 4 wherein said control means include a flexible shaft within said tubular body coupled at its distal end to said threaded rod and at its proximal end to a control knob.

9. The device of claim 8 wherein said flexible shaft has a knob mounted on the proximal end thereof.

10. The device of claim 9 wherein the proximal end of said tubular body or said knob has calibration markings and said knob or said proximal end of said tubular body has an indicator relative to the calibration marking indicating the extent of expansion of said flexible expandable tubular member.

11. The device of claim 4 wherein said mechanism includes a hub mounted within the hollow distal end of said tubular body, and the proximal end of said threaded portion of said rod is journalled in said hub.

12. The device of claim 10 wherein said threaded rod is journalled at its distal end to a bracket in said tip member.

13. The device of claim 4 wherein said tubular body has a diameter approximately one-third the diameter of a blood vessel in which it is received.

14. The device of claim 4 wherein said tubular body has a diameter between approximately 1 mm and 3 mm.

15. The device of claim 14 wherein said tubular body has a diameter of approximately 1.35 mm.

16. The device of claim 4 wherein said flexible expandable tubular member is expandable from a diameter between 1 mm and 4.0 mm to a diameter between 2.3 mm and 9.0 mm when expanded.

17. The device of claim 16 wherein said non-expanded diameter of said flexible expandable tubular member is approximately 1.35 mm.

18. The device of claim 16 wherein said non-expanded diameter of said flexible expandable tubular member is approximately 2.3 mm.

19. The device of claim 4 wherein said flexible expandable tubular member is made of a biocompatible polymer.

20. The device of claim 19 wherein said polymer is polyurethane.

21. The device of claim 19 wherein said flexible expandable tubular member has a wall thickness of approximately 0.002 mm.

22. The device of claim 7 wherein said tubular body is thick walled with a lumen therethrough of sufficient cross section to receive said flexible rotatable shaft therein.

* * * * *